(12) United States Patent
Kirsch et al.

(10) Patent No.: US 9,770,309 B2
(45) Date of Patent: Sep. 26, 2017

(54) SHAFT OF A DENTAL TOOL

(71) Applicant: Gebr. Brasseler GmbH & Co. KG, Lemgo, DE (US)

(72) Inventors: Axel Kirsch, Stuttgart (DE); Walter Duerr, Remchingen-Noettingen (DE); Volker Brinkmann, Lemgo (DE); Karl-Heinz Danger, Detmold (DE)

(73) Assignee: GEBR. BRASSELER GMBH & CO. KG, Lemgo (DE)

( * ) Notice: Subject to any disclaimer, the term of this patent is extended or adjusted under 35 U.S.C. 154(b) by 0 days.

(21) Appl. No.: 14/655,768

(22) PCT Filed: Dec. 19, 2013

(86) PCT No.: PCT/EP2013/077516
§ 371 (c)(1),
(2) Date: Jun. 26, 2015

(87) PCT Pub. No.: WO2014/111227
PCT Pub. Date: Jul. 24, 2014

(65) Prior Publication Data
US 2015/0359607 A1    Dec. 17, 2015

(30) Foreign Application Priority Data
Jan. 21, 2013 (DE) .......... 10 2013 000 956

(51) Int. Cl.
A61C 1/18    (2006.01)
A61C 3/02    (2006.01)
(Continued)

(52) U.S. Cl.
CPC ............... *A61C 1/18* (2013.01); *A61C 1/141* (2013.01); *A61C 3/02* (2013.01); *A61C 8/0089* (2013.01)

(58) Field of Classification Search
CPC ....... A61C 5/02; A61C 17/24; A61C 17/3409; A61C 1/18
See application file for complete search history.

(56) References Cited

U.S. PATENT DOCUMENTS

| 5,017,137 A | 5/1991 | Weissman |
| 5,105,690 A * | 4/1992 | Lazzara ............... A61C 8/0089 81/436 |

(Continued)

FOREIGN PATENT DOCUMENTS

| DE | 202008017281 | 4/2009 |
| GB | 252343 | 7/1927 |

(Continued)

OTHER PUBLICATIONS

International Search Report dated Mar. 24, 2014 for related app. No. PCT/EP2013/077516.

*Primary Examiner* — Michael Carey
*Assistant Examiner* — Natasha Patel
(74) *Attorney, Agent, or Firm* — Shuttleworth & Ingersoll, PLC; Timothy J. Klima

(57) ABSTRACT

The present invention refers to a shaft of a dental tool comprising a distal end region, a cylindrical shaft region adjoining the distal end region, and a proximal end region which lies opposite the distal end region and which is provided with a polygonal profile that tapers conically in the direction of the distal end region and adjoins a tool part.

16 Claims, 4 Drawing Sheets

(51) Int. Cl.
*A61C 1/14* (2006.01)
*A61C 8/00* (2006.01)

(56) References Cited

U.S. PATENT DOCUMENTS

| | | | | |
|---|---|---|---|---|
| 5,277,531 A * | 1/1994 | Krivec | ............... | B25B 13/065 411/403 |
| 5,989,026 A * | 11/1999 | Rogers | ............... | A61C 8/005 433/172 |
| 6,168,435 B1 * | 1/2001 | Beaty | ............... | A61C 8/005 433/172 |
| 8,029,282 B2 * | 10/2011 | Carter | ............... | A61C 8/0089 433/141 |
| 2013/0004916 A1 * | 1/2013 | Bellanca | ............... | A61C 8/0018 433/173 |

FOREIGN PATENT DOCUMENTS

| | | |
|---|---|---|
| GB | 1554006 | 10/1979 |
| WO | 2009014746 | 1/2009 |

\* cited by examiner

SHAFT OF A DENTAL TOOL

This application is the National Phase of International Application PCT/EP2013/077516 filed Dec. 19, 2013 which designated the U.S.

This application claims priority to German Patent Application No. DE102013000956.1 filed Jan. 21, 2013, which application is incorporated by reference herein.

The present invention refers to a shaft of a dental tool which can be clamped in a drive device, for example an angle piece.

The shaft of a dental tool serves to detachably fasten the dental tool (for example a drill, or the like) to an angle piece in such a manner that a torque transmission is particularly ensured. Furthermore, the shaft serves to exactly guide the dental tool and to ensure a centered smooth movement of the dental tool upon rotation of the dental tool about its center axis. The shaft must be configured such that the shaft can be inserted easily and simply into the drive device, for instance the angle piece, and the dental tool can be removed again analogously in a simple manner. It should particularly be considered that the user, e.g. a dentist, is able to insert and remove the shaft with ease in a surgical or preparatory environment.

The prior art already discloses shaft constructions according to ISO-1797. These are the normally used designs. The shaft is here provided on its distal end region with a flattening which is in positive engagement with a corresponding force-transmitting surface of the drive mechanism. In addition, the shaft may be provided on its distal end region with a recess or an annular groove, or the like, to provide an axial lock.

It is the object of the present invention to create a shaft of the aforementioned type which while being of a simple construction and easily producible at low costs exhibits a high degree of operational safety and functionality.

This object is achieved by the features described herein.

Hence, according to the invention the shaft of a dental tool is created that comprises a distal end region and a cylindrical shaft region adjoining the distal end region. Opposite the distal end region, a proximal end region is formed on the shaft and adjoined by the dental tool. The shaft is integrally connected to the dental tool; the dental tool may here be made from the same material as the shaft, or different materials may be connected by means of a joining method.

Furthermore, according to the invention it is provided that the proximal end region is provided with a polygonal profile. In a particularly advantageous design of the invention it is provided that the polygonal profile tapers conically in the direction of the distal end region.

The design of the shaft according to the invention offers many advantages. While in the shaft constructions known from the prior art the torque is introduced on the distal end region, it is provided according to the invention that the polygonal profile through which the torque from the drive element (angle piece) is introduced is configured in the form of a polygonal profile directly adjoining the tool part. This offers the decisive advantage that the effective length of the shaft that is under torsional stress is minimized. Hence, the torque is introduced directly next to the tool part, whereas the remaining shaft is not under torsional stress. It just serves to guide and center the tool part or the dental tool, respectively, and serves axial fixation.

Hence, the shaft according to the invention can be used in an efficient manner in a drive mechanism for transmitting the drive element or torque to the dental tool. This offers a further advantage with respect to the bending forces acting on the shaft. Since such a shaft is always supported with a certain play in the drive element, one is also confronted with bending forces that do not always guarantee an exact centering of the tool part, in the case of the designs known from the prior art and in addition to the torsional moments. These bending forces lead to an irregular or uneven running of the tool part and thus to a reduced precision of the drilling function or cutting function of the tool part. Especially in the case of implant bed drills this may have a negative impact because the drilled holes may become non-round, so that an implant does not have the desired firm seat. According to the invention the bending forces are minimized because torque transmission takes place directly next to the tool part.

A further essential advantage of the present invention is that the polygonal profile ensures a clearance-free seat or fit in the drive mechanism owing to its conical taper. Hence, the shaft is received in the drive element in a self-centered manner and without clearance. Especially upon rotations in different rotational directions or upon different loads during the axial advance movement of the dental tool, a clearance-free safe fixation thereby takes place. In addition to the safe fixation, this offers the advantage that the conical shape produces a clamping in axial direction, so that the polygonal profile is effective not only in terms of torque transmission, but also in terms of axial locking.

Thus, owing to the construction according to the invention, the shaft has a much higher polar resistance moment. In comparison with the shaft constructions known from the prior art, it is up to 84% higher. In the case of a polygonal profile which is configured as a hexagon with a width across flats of 2.5 mm, this yields e.g. a polar resistance element of 2.94 mm3. If the shaft is provided with a centric bore for internal cooling, one obtains a polar resistance moment of about 2.5 mm3.

The conically tapering polygonal profile according to the invention has for instance a conical envelope on which the edges between the neighboring flattened portions of the polygonal profile are positioned. Hence, according to the invention, the flanks of the polygonal profile are arranged preferably inclined relative to the center axis of the shaft.

As has been mentioned, the polygonal profile according to the invention may be designed as a hexagonal profile. However, it is also possible to provide other profiles in symmetry with the center axis (axis of rotation, pivot axis), e.g. a bi-hex profile or an octagonal profile.

With the invention it is also possible to considerably reduce the total length of the shaft. Since the torque is introduced directly adjacent to the tool part, the remaining shaft length must just be so great that the shaft on the whole is supported in rotation symmetry with its center axis. Depending on the dimensions, this can also be carried out with a very short shaft that is much shorter than the shaft lengths known from the prior art.

According to the invention the tool part, as has been mentioned, may be configured in the form of an implant bed drill. However, it is also possible according to the invention to implement different drill forms. Further different forms of the tool part are also possible, e.g. millers, countersinks, thread cutters, or grinding tools.

In a particularly advantageous design of the invention the shaft may also be provided with a substantially tubular extension attachment which forms the tool part. This makes it possible to implement a drill extension by means of the shaft. Preferably, the tubular extension attachment is provided on its free end region with an internal contour the shape of which is configured to match the conically tapering polygonal profile. Hence, a further shaft of a dental tool can be inserted into the drill extension. This also yields especially the above-mentioned advantages regarding clearance-free support and high torsional strength.

According to the invention the polygonal profile may be configured to be conical either over its total length or just over part of its axial length.

Further advantages are achieved with respect to the manufacture of the shaft according to the invention. Since the polygonal profile is configured to be substantially in rotation symmetry with the center axis, this makes it possible to produce the entire shaft by means of a turning process. The application of asymmetrical milling operations or the like is not required, as is needed in the prior art. This also leads to an increased precision of the shaft according to the invention.

Furthermore, it is possible according to the invention to use suitable materials for the shaft, e.g. hardened or unhardened steels. Since the polygonal profile is mechanically loaded to a much smaller degree than the flattening known from the prior art for transmitting the torque, less demands are made on wear.

The torsion acting on the shaft is thus dependent on the effective length of the shaft between the torque introduction region and the region on which the cutting forces are acting. Since according to the invention the torque is introduced proximal to the tool part, the effective shaft length that is subjected to torsion is much smaller. Likewise, the shaft length influences the lateral deflection and thus the impact of an instrument. Thus the solution according to the invention leads to an improved static and dynamic arrangement. It must here also be considered that both axial forces and lateral forces are applied in the case of manual drilling. Thanks to the construction according to the invention the lateral forces result in less deflection and thus increased precision of the machining process.

With the design of the tool part according to the invention in the form of an implant bed drill, the improved true-running accuracy or concentricity and the increased polar resistance moment have particularly advantageous effects. Drives for implant bed drills are normally equipped with a torque limitation. Hence, it may happen that during surgical use the drive is repeatedly switched on and off. This results in vibrations and in deformations in the plastic area of the material. The design of the shaft according to the invention is here distinguished by a considerably increased strength. This results in an increased precision of the machining operation. It must further be considered that the implant bed drill may get caught in a patient's irregular bone structure. This results in stress peaks which enable fractures on the drill. According to the invention the stress peaks occur next to the polygonal profile, so that the remaining shaft is not affected. Hence, in case of a fracture of the drill, the remaining shaft can easily be removed from the angle piece. This is not possible in the constructions known from the prior art.

The invention will now be described with reference to embodiments taken in conjunction with the drawing, in which.

Figure 1:
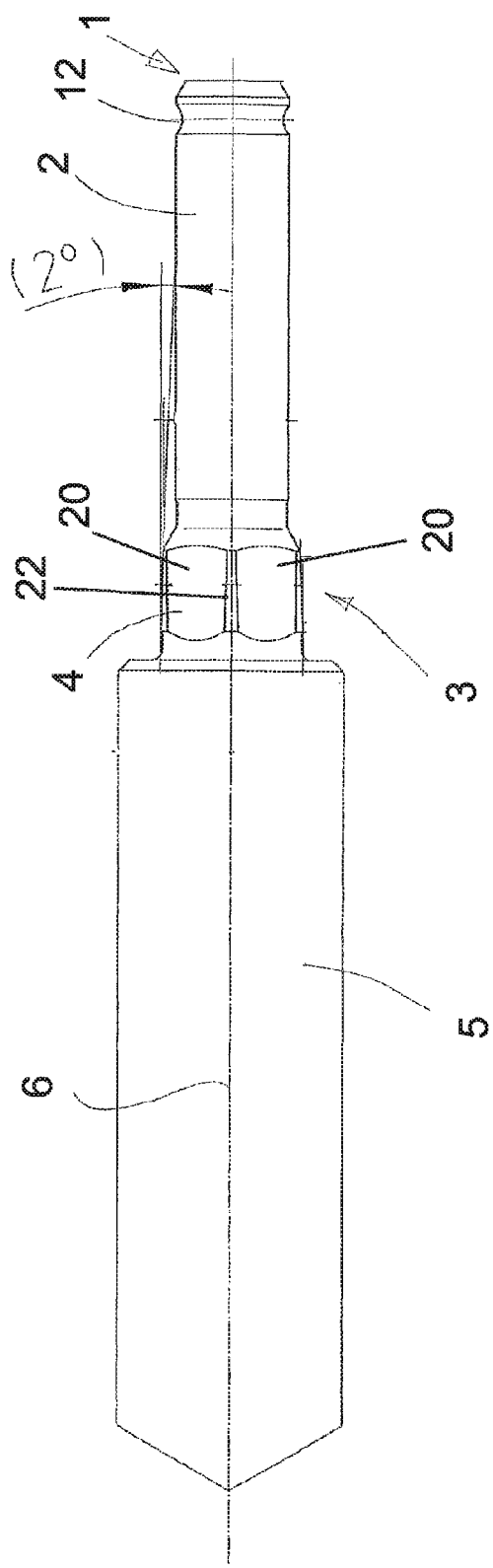
FIG. 1 is a schematic side view of a first embodiment of the shaft according to the invention.
Figure 2:
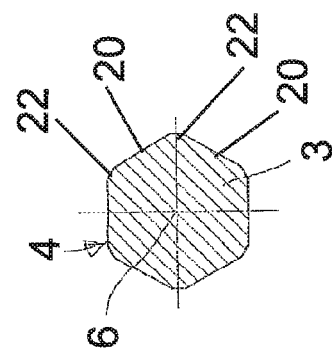
FIG. 2 is a sectional view through the polygonal profile.

FIG. 1 shows a shaft of the invention which comprises a distal end region 1. This region is integrally adjoined by a cylindrical shaft region 2. This region, in turn, passes into a proximal end region 3. The proximal end region 3 is configured as a polygonal profile. In the embodiment shown in FIG. 1, this profile is a hexagonal profile, as shown in FIG. 2. The polygonal profile includes a plurality of flanks 20 joined at corners 22, which corners 22 can be radiused or relieved, as shown, for example, in FIGS. 1-2 and 7-8. The polygonal profile 4 is adjoined by a tool part 5. The tool part 5 is e.g. configured in the form of an implant bed drill, as is known from the prior art, or in the form of a shaft extension (extension attachment) 7, as will be described hereinafter in connection with FIGS. 3 to 6. FIG. 9 shows a portion of a drive element 20, including a torque introduction piece 22 positioned adjacent the polygonal profile 4 and shaped to engage the polygonal profile 4 and rotationally drive the shaft via the polygonal profile 4. The drive element 20 also includes a centering piece 24 positioned adjacent the distal end region 1 and shaped to engage the distal end region 1 for centering the distal end region 1.

The polygonal profile is given a conical shape over its whole length in the embodiment of FIGS. 1 and 2, a cone angle of 2° being provided here.

Reference numeral 6 designates the center axis or rotation axis.

The embodiment shows that the diameter of the cylindrical shaft region 2 may be smaller than the diameter of the polygonal profile because the cylindrical shaft region 2 does not serve torque transmission. Accordingly, the transition region between the polygonal profile 4 and the tool part 5 may be given a large diameter size so as to have a high resistance moment. The polygonal profile 4 directly adjoins the tool part 5.

Figure 3:
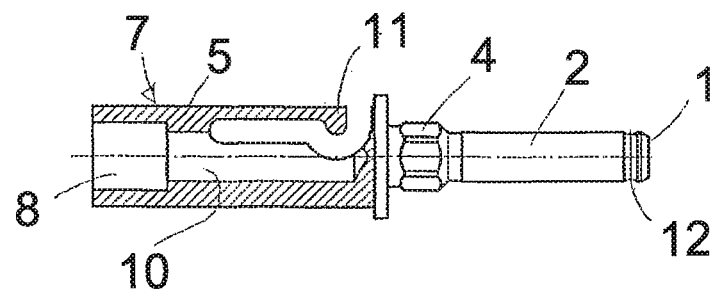
FIG. 3 shows an embodiment in which the tool part is configured as a shaft extension.
Figure 7:
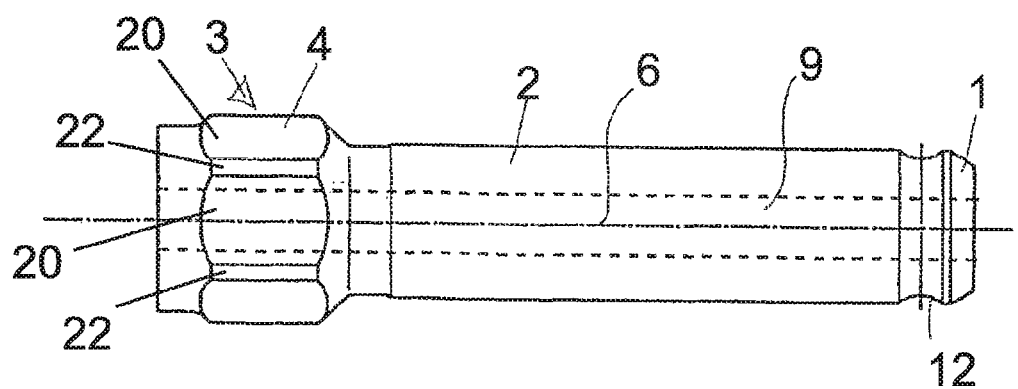
FIGS. 7 and 8 show positions, by analogy with FIGS. 1 and 2, of an embodiment with internal cooling.
Figure 8:
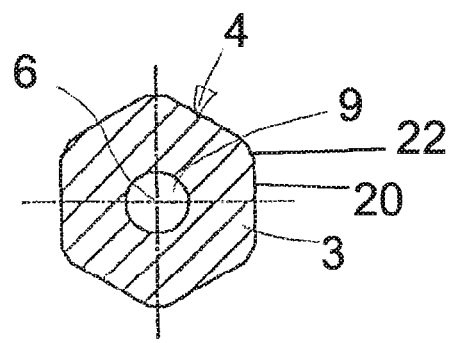
Figure 9:
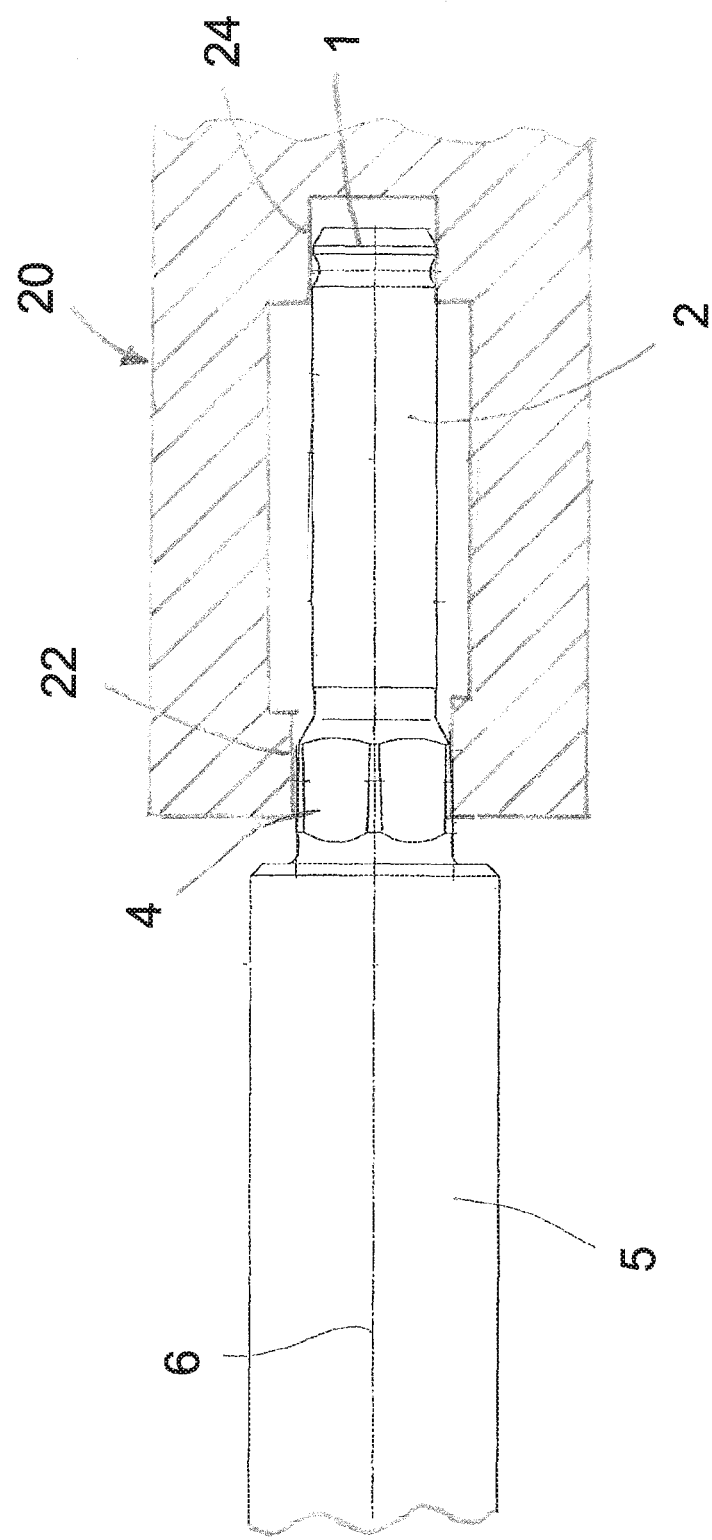
FIG. 9 shows a dental tool drive system including a shaft and drive element.

FIGS. 7 and 8 show a similar design as FIGS. 2 and 3. A centric cooling channel 9 is additionally provided.

Figure 4:
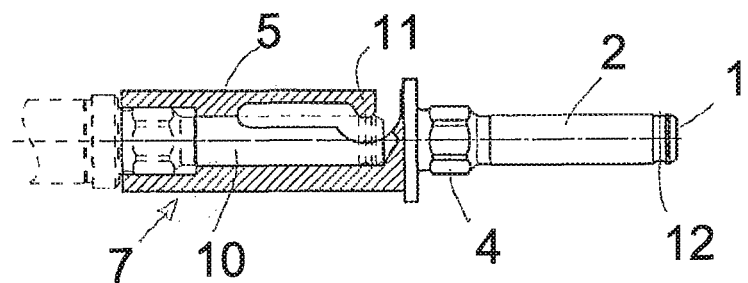
FIG. 4 is a side view, by analogy with FIG. 3, with inserted further shaft.
Figure 5:
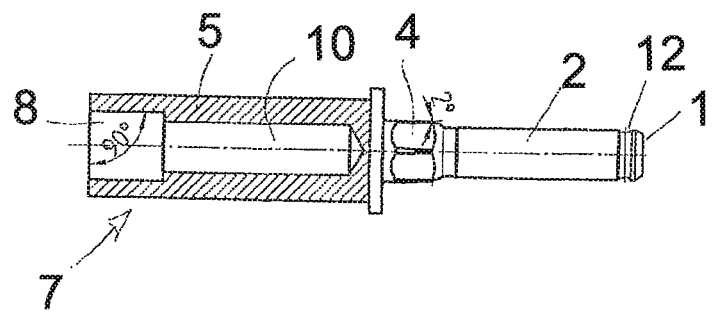
FIGS. 5 and 6 are illustrations, by analogy with FIGS. 3 and 4, in a changed design of the tool part as shaft extension.
Figure 6:
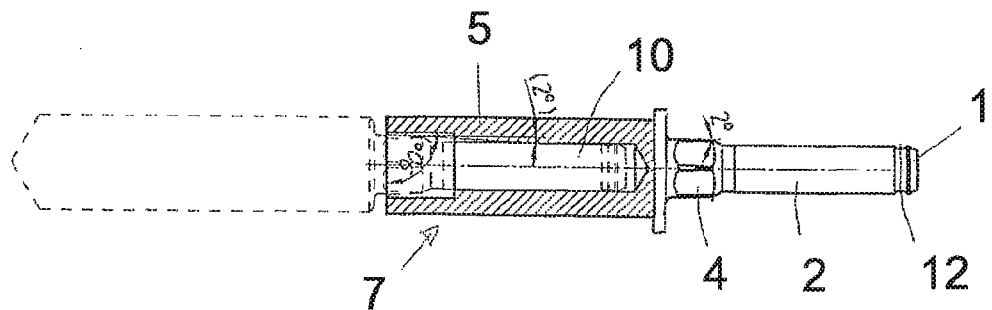

In the embodiment of FIGS. 3 to 6, the tool part 5 is each time configured as a tubular shaft extension. The remaining designs of the shaft are each substantially the same as in the embodiment of FIGS. 1 and 2. The shaft extension has a centric recess 10 into which a further shaft can be inserted, as is shown in FIGS. 4 and 6. The free end has provided thereon the centric recess 10 with an internal contour 8 which is also configured in the form of a conical polygonal profile to fit the polygonal profile 4. In the embodiment of FIGS. 3 and 4 an elastic locking element 11 is provided, which is e.g. already known from DE 20 2008 017 281 U1.

In all embodiments, an annular groove 12 that serves additional axial locking is provided on the distal end region 1.

LIST OF REFERENCE NUMERALS 1 distal end
2 cylindrical shaft region
3 proximal end region
4 polygonal profile
5 tool part
6 center axis
7 shaft extension (extension attachment)
8 internal contour
9 centric cooling channel
10 centric recess 11 locking element
12 annular groove

The invention claimed is:

1. A shaft of a dental tool comprising:
   a distal end region,
   a shaft region adjoining the distal end region, and
   a proximal end region which lies opposite the distal end region and which includes a polygonal profile, the polygonal profile including a plurality of flanks forming, at a same axial position on the proximal end region, an outer periphery of the proximal end region, all of the plurality of flanks tapering radially inwardly in a direction toward the distal end region and being directly exposed to the distal end region, the proximal end region adjoining a tool part;
   wherein the tool part is configured as a substantially tubular extension attachment;
   wherein the tubular extension attachment includes, on a free end region thereof, an internal contour formed as a pyramid frustum polygonal profile.

2. The shaft according to claim 1, wherein the polygonal profile has a pyramid frustum envelope.

3. The shaft according to claim 1, wherein the plurality of flanks of the polygonal profile are arranged inclined to a center axis of the shaft.

4. The shaft according to claim 1, wherein the polygonal profile is configured as a hexagonal profile and the shaft region is cylindrical.

5. The shaft according to claim 1, wherein the tool part is configured as an implant bed drill.

6. The shaft according to claim 1, wherein the distal end region includes an annular groove.

7. The shaft according to claim 1, wherein the polygonal profile has a pyramid frustum profile over a total axial length of the polygonal profile.

8. The shaft according to claim 1, and further comprising radiused corners positioned between adjacent flanks of the polygonal profile.

9. The shaft according to claim 1, wherein corners between adjacent flanks of the polygonal profile are relieved.

10. The shaft according to claim 1, wherein the distal end region includes an annular groove.

11. The shaft according to claim 1, wherein the polygonal profile has a pyramid frustum profile over a total axial length of the polygonal profile.

12. A dental tool drive system, comprising:
    a shaft, including:
       a distal end region,
       a shaft region adjoining the distal end region, and
       a proximal end region which lies opposite the distal end region and which includes a polygonal profile, the proximal end region adjoining a tool part, the proximal end region tapering radially inwardly in a direction toward the distal end region,
    a drive element, including:
       a torque introduction piece positioned adjacent the polygonal profile and shaped to engage the polygonal profile and rotationally drive the shaft via the polygonal profile,
    a centering piece positioned adjacent the distal end region and shaped to engage the distal end region for centering the distal end region;
       wherein the torque introduction piece includes, on a free end region thereof, an internal contour formed as a pyramid frustum polygonal profile.

13. The dental tool drive system according to claim 12, wherein the shaft region positioned between the distal end region and the proximal end region has a minimum cross-sectional width smaller than a minimal cross-sectional width of the polygonal profile.

14. The dental tool drive system according to claim 12, wherein the polygonal profile includes a plurality of flanks forming, at a same axial position on the proximal end region, an outer periphery of the proximal end region, all of the plurality of flanks tapering radially inwardly in the direction toward the distal end region and being directly exposed to the distal end region.

15. The shaft according to claim 14, wherein the plurality of flanks of the polygonal profile are arranged inclined to a center axis of the shaft.

16. The shaft according to claim 12, wherein the polygonal profile has a pyramid frustum envelope.

* * * * *